United States Patent [19]

Guyon

[11] Patent Number: 5,523,469

[45] Date of Patent: Jun. 4, 1996

[54] OPTICALLY ACTIVE ALKYLAMMONIUM 1-(3-AMINOPHENYL)-ETHANESULPHONATE DERIVATIVES, THEIR PREPARATION AND THEIR USE

[75] Inventor: Claude Guyon, Saint Maur Des Fosses, France

[73] Assignee: Rhone-Poulenc Rorer S.A., Antony, France

[21] Appl. No.: 397,045

[22] PCT Filed: Sep. 6, 1993

[86] PCT No.: PCT/FR93/00849

§ 371 Date: Mar. 10, 1995

§ 102(e) Date: Mar. 10, 1995

[87] PCT Pub. No.: WO94/06760

PCT Pub. Date: Mar. 31, 1994

[30] Foreign Application Priority Data

Sep. 11, 1992 [FR] France .................................. 92 10840

[51] Int. Cl.⁶ .................................................. C07C 309/29

[52] U.S. Cl. ............................ 562/41; 540/489; 548/146; 548/400; 546/184; 546/348

[58] Field of Search ............................... 562/41; 540/489; 548/146, 400; 546/184, 348

[56] References Cited

U.S. PATENT DOCUMENTS 3,883,502  5/1975  Sommer et al. .

FOREIGN PATENT DOCUMENTS 2132818  11/1972  France .
WO91/13907  9/1991  WIPO .

*Primary Examiner*—José G. Dees
*Assistant Examiner*—Joseph M. Conrad, III
*Attorney, Agent, or Firm*—Finnegan, Henderson, Farabow, Garrett & Dunner

[57] ABSTRACT

This invention relates to levogyral isomers of alkylammonium (amino-3 phenyl)-1 ethanesulphonate derivatives of formula (I) in which R+ denotes a tetraalkylammonium or trialkylphenylalkylammonium residue. The invention also concerns the preparation and use of said derivatives.

17 Claims, No Drawings

OPTICALLY ACTIVE ALKYLAMMONIUM 1-(3-AMINOPHENYL)-ETHANESULPHONATE DERIVATIVES, THEIR PREPARATION AND THEIR USE

DESCRIPTION OF THE INVENTION

The present invention relates to the laevorotatory isomers of alkylammonium 1-(3-aminophenyl)ethanesulphonates of formula:

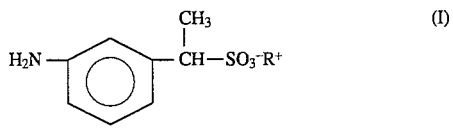

in which $R^+$ represents a tetraalkylammonium or trialkylphenylalkylammonium residue, to their preparation and their use as intermediates in the preparation of compounds which are useful as cholecystokinin (CCK) and gastrin antagonists.

In the preceding definitions, and in those which follow, the alkyl radicals contain 1 to 4 carbon atoms in a straight or branched chain. They preferably represent the n-butyl radical.

The compounds of formula (I) (laevorotatory isomers) can be prepared in accordance with the following process:

a) action of an alkali metal sulphite on (RS)-1-(1-bromoethyl)-3-nitrobenzene and, if necessary, conversion to the potassium salt to give potassium (RS)-1-(3-nitrophenyl)ethanesulphonate, b) conversion of the potassium salt obtained in a) into a mixture of the A and B forms of benzylquininium 1-(3-nitrophenyl)ethanesulphonate, separation of the A form and recovery of a mixture enriched in the B form, c) conversion of the benzylquininium salt, enriched in the B form, obtained in b) into potassium 1-(3-nitrophenyl)ethanesulphonate, thereafter into phenylglycinol 1-(3-nitrophenyl)ethanesulphonate, B form, and finally into the tetraalkylammonium or trialkylphenylalkylammonium 1-(3-nitrophenyl)-ethanesulphonate (laevorotatory isomer)

d) reduction of the product obtained in c) to give the compound of formula (I) (laevorotatory isomer).

It is particularly advantageous to carry out stage a) in aqueous solution at a temperature of between 50° C. and 100° C. and preferably at 80° C.

The alkali metal sulphite is preferably sodium sulphite or potassium sulphite.

To recover the product, it is preferable to convert it to the tetraalkylammonium or trialkylphenylammonium salt, isolate this and then convert it to the potassium salt.

Stage b) is preferably carried out by means of an N-benzylquininium halide, and preferably the chloride, in the presence of potassium dihydrogenphosphate in an aqueous medium and at a temperature of between 10° C. and 30° C. in particular at a temperature of about 20° C.

The potassium salt of stage c) is obtained by treatment with potassium nonafluorobutanesulphonate, in an inert solvent such as acetone, at a temperature of between 10° C. and 30° C., and preferably at 20° C.

The phenylglycinol salt of stage c) is obtained by treatment with (R)-(-)-phenylglycinol in the presence of an acid such as hydrochloric acid, in an aqueous medium, at a temperature of between 10° C. and 30° C. and preferably at 20° C.

The phenylglycinol salt is thereafter converted to the compound of formula (I) by means of a tetraalkylammonium or trialkylphenylalkylammonium salt, preferably the hydrogensulphates, in an aqueous medium, at a temperature of between 10° C. and 30° C. and preferably at 20° C.

The reduction of stage d) is generally carried out under hydrogen pressure, in the presence of a hydrogenation catalyst such as palladium, in an inert solvent such as an alcohol (for example ethanol), at a temperature of about 25° C. Preferably, a hydrogen pressure of 100 kPa is used.

The compounds of formula (I) (laevorotatory isomers) are particularly valuable as intermediates for the preparation of the enantiomers of the compounds of formula:

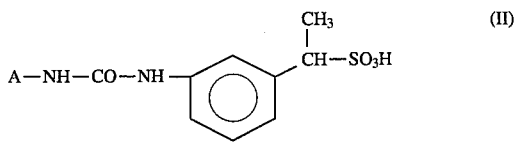

and their salts.

In formula (II), A represents:

A) a $-CH_2-CO-NR_1R_2$ residue, in which $R_1$ represents one of the following radicals: (a) phenyl optionally substituted by one or more substituents chosen from among halogen atoms and alkyl, alkoxy, hydroxyl polyfluoroalkyl, nitro, alkylthio, alkoxycarbonyl, carboxyl, acylamino, methylenedioxy, polyfluoroalkoxy, trifluoromethylthio, phenoxy, phenyl, benzyl, phenylamino and $CONR_3R_4$ radicals, which may be identical or different, represent a hydrogen atom or an alkyl, phenyl (optionally substituted by one or more substituents chosen from among halogen atoms and alkyl, alkoxy and alkylthio radicals), indanyl, cycloalkylalkyl, cycloalkyl or phenylalkyl radical or else $R_3$ and $R_4$ together with the nitrogen atom to which they are attached form a saturated or unsaturated monocyclic or polycyclic heterocyclic ring containing 4 to 9 carbon atoms and one several heteroatoms (O, N or S) and optionally substituted by one or several alkyl, alkoxy, alkoxycarbonyl, dialkylcarbamoyl or phenyl radicals or, in combination with a carbon atom of the heterocyclic ring, by a spiromonocyclic ring having 4 or 5 members and optionally containing one or more heteroatoms (O, S or N); b) pyridyl, c) isoquinolyl, d) quinolyl, e) quinoxalinyl (these heterocyclic rings being optionally substituted by one or more substituents chosen from among alkyl and phenyl radicals and halogen atoms), f) alkyl, g) phenylalkyl, h) naphthyl, i) 5,6,7,8-tetrahydronaphthyl, j) 1,2,3,4-tetrahydronaphthyl, k) alkoxycarbonylalkyl or l) cycloalkyl. $R_2$ represents a $-CH(R_5)-CO-R_6$ chain in which $R_5$ represents a hydrogen atom or an alkyl or alkoxycarbonyl radical or a phenyl radical (optionally substituted by one or more substituents chosen from among halogen atoms and alkyl, alkoxy, alkylthio, nitro and amino radicals), and $R_6$ represents an alkoxy, cycloalkoxy (optionally substituted by at least one alkyl radical), cycloalkylalkoxy, phenylalkoxy, polyfluoroalkoxy cinnamyloxy radical and $-NR_3R_4$.

B) a residue of formula:

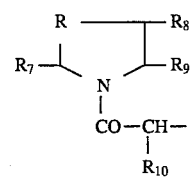

in which:

either R represents a methylene, ethylene, SO, $SO_2$ or CHOH radical or a sulphur atom, $R_7$ represents a pyridyl radical optionally substituted by one or more alkyl radicals, a furyl radical optionally substituted by one or more alkyl radicals, a thienyl radical optionally substituted by one or more alkyl radicals, a quinolyl radical optionally substituted by one or more alkyl radicals, a naphthyl radical optionally substituted by one or more alkyl radicals, an indolyl radical optionally substituted by one or more alkyl radicals or phenyl optionally substituted by one or more substituents chosen from among halogen atoms and alkyl, alkoxy, hydroxyl, nitro, amino, monoalkylamino, dialkylamino, alkoxycarbonyl, —CO—NR$_{11}$R$_{12}$, —NH—CO—CH$_3$, trifluoromethyl or trifluoromethoxy radicals and R$_8$ represents a hydrogen atom, or R represents a methylene radical, R$_7$ represents a hydrogen atom and R$_8$ represents a phenyl radical, or R represents a CHR$_{13}$ radical, and R$_7$ and R$_8$ each represent a hydrogen atom, R$_9$ represents an alkoxycarbonyl, cycloalkoxycarbonyl, cycloalkylalkoxycarbonyl or —CONR$_{14}$R$_{15}$ radical or a phenyl radical optionally substituted by one or more substituents chosen from among alkyl, alkoxy or hydroxyl radicals, R$_{10}$ represents a hydrogen atom or an alkyl radical, R$_{13}$ represents a phenyl radical, R$_{11}$ represents a hydrogen atom or one of the following radicals: alkyl, phenylalkyl or phenyl optionally substituted by one or more substituents chosen from among halogen atoms and alkyl, alkoxy and alkylthio radicals, R$_{12}$ represents one of the following radicals: alkyl, phenylalkyl or phenyl optionally substituted by one or more substituents chosen from among halogen atoms and alkyl, alkoxy and alkylthio radicals, or else R$_{11}$ and R$_{12}$, together with the nitrogen atom to which they are attached, form a monocyclic or polycyclic, saturated or unsaturated, heterocyclic ring which contains 4 to 9 carbon atoms and one or more heteroatoms (O or N) and is optionally substituted by one or more alkyl radicals, R$_{14}$ represents a hydrogen atom or one of the following radicals: alkyl, cycloalkylalkyl, cycloalkyl, phenylalkyl or phenyl optionally substituted by one or more substituents chosen from among halogen atoms and alkyl, alkoxy and alkylthio radicals, R$_{15}$ represents one of the following radicals: alkyl, cycloalkylalkyl, cycloalkyl, phenylalkyl or phenyl optionally substituted by one or more substituents chosen from among halogen atoms and alkyl, alkoxy and alkylthio radicals, or else R$_{14}$ and R$_{15}$ together with the nitrogen atom to which they are attached form a monocyclic or polycyclic, saturated or unsaturated, heterocyclic ring which contains 4 to 9 carbon atoms and one or more heteroatoms (O, N or S) and is optionally substituted by one or more alkyl radicals, C) a residue of formula:

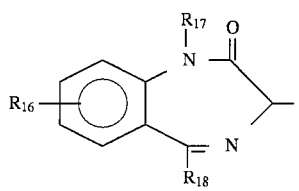

in which:

R$_{16}$ represents a hydrogen or halogen atom or an alkyl, alkylthio, nitro, hydroxyl or cyano radical, R$_{17}$ represents an alkyl radical or a —CH(R$_5$)—CO—R$_6$ residue, R$_{18}$ represents a pyridyl radical or phenyl radical optionally substituted by one or more substituents chosen from among halogen atoms and alkyl, alkoxy, hydroxyl, carboxyl, and nitro radicals.

In the definitions of the compounds of formula (II), the alkyl and alkoxy radicals and the alkyl and alkoxy moieties preferably contain 1 to 4 carbon atoms in a straight or branched chain, the cycloalkyl radicals and moieties 3 to 6 carbon atoms and the acyl radicals 2 to 4 carbon atoms.

These compounds are described in Patent Applications WO 91/12264, WO 91/13907, WO 91/13874, FR 9108675 and FR 9112481 as being antagonists for cholecystokinin and gastrin.

The compounds of formula (II) can be prepared from the compounds of formula (I) by proceeding as follows:

a compound of formula (I) is caused to act on a derivative of formula:

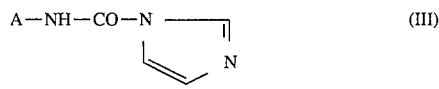

in which a has the same meanings as in formula (II).

This reaction is generally carried out in an inert solvent such as tetrahydrofuran, dimethylformamide, a chlorinated solvent or an aromatic solvent (for example benzene or toluene), at a temperature of between 20° C. and the boiling point of the solvent.

The derivatives of formula (III) can be prepared in accordance with the processes described in Patent Applications WO 91/12264, WO 91/13907, WO 91/13874, FR 9108675 and FR 9112481.

EXAMPLES

EXAMPLE 1 a) potassium (RS)-1-(3-nitrophenyl)ethanesulphonate:

25.3 g of (RS)-1-(1-bromoethyl)-3-nitrobenzene are added to a solution of 20.8 g of sodium sulphite in 260 cm$^3$ of water. The reaction mixture is stirred at 80° C. for 5 hours, cooled to about 25° C. and run into 2.5 liters of an aqueous 0.5M potassium dihydrogenphosphate solution, to which 40 g of tetra-n-butylammonium hydrogen sulphate are added. The mixture is extracted with 3 times 500 cm$^3$ of methylene chloride. The combined organic phases are washed with twice 500 cm$^3$ of water, dried over magnesium sulphate and concentrated to dryness under reduced pressure (2.7 kPa) at 40° C. The oil obtained is dissolved in 65 cm$^3$ of acetone and 34 g of potassium nonafluorobutanesulphonate dissolved in 75 cm$^3$ of acetone are added. The insoluble product is filtered off, washed with 3 times 50 cm$^3$ of diisopropyl ether and dried in air. 22.4 g of potassium (RS)-1-(3-nitrophenyl)ethanesulphonate, melting at a temperature above 260° C., are thus obtained and are used as such in the subsequent syntheses.

| NMR spectrum: (200 MHz; DMSO d) δ (ppm): | |
|---|---|
| 1.50 | [d, J=7 Hz, 3H: —CH(C$\underline{H}_3$)—] |
| 3.93 | [q, J=7 Hz, 1H: —C$\underline{H}$(CH$_3$)—] |
| 7.59 | [t, J=8 Hz, 1H: —C$_6$H$_4$(—$\underline{H}$5)] |
| 7.83 | [d, J=8 Bz, 1H: —C$_6$H$_4$(—$\underline{H}$6)] |

-continued

NMR spectrum: (200 MHz; DMSO d)
δ (ppm):

| 8.10 | [broad d, J=8 Hz, 1H: —C₆H₄(—H4)] |
| 8.26 | [broad s, 1H: —C₆H₄(—H2)] |

(RS)-1-(1-Bromoethyl)-3-nitrobenzene can be prepared in accordance with the method described by E. Felder et al., J. Med. Chem., 13, 559 (1970).

b) mixture of the A and B forms of N-benzylquininium 1-(3-nitrophenyl)ethanesulphonate:

87 g of potassium dihydrogenphosphate and 32.4 g of N-benzylquininium chloride are added to a solution of 17.2 g of potassium (RS)-1-(3-nitrophenyl)ethanesulphonate in 400 cm³ of water. The mixture is extracted with twice 300 cm³ of methylene chloride. The combined organic phases are washed with twice 200 cm³ of water, dried over magnesium sulphate and concentrated to dryness under reduced pressure (2.7 kPa)) at 40° C. The froth obtained is dissolved in 120 cm³ of 2-propanol under reflux. After cooling, the crystals are filtered off and washed with twice 15 cm³ of 2-propanol. After 2 recrystallizations, from 350 and then from 500 cm³ of 2-propanol, 15.6 g of the A form of N-benzylquininium 1-(3-nitrophenyl)ethanesulphonate are obtained, melting at about 110° C. $[\alpha]_D^{20}$=−151.3°±1.5 (C=1.009%; methanol). The propanol solutions are combined and concentrated to dryness under reduced pressure (2.7 kPa) at 45° C. 25.0 g of a mixture of the A and B forms (about 15/85 in moles) of N-benzylquininium 1-(3-nitrophenyl)ethanesulphonate are thus obtained.

c) laevorotatory isomer of tetra-n-butylammonium 1-(3-nitrophenyl)ethanesulphonate:

5.2 g of potassium nonafluorobutanesulphonate dissolved in 12 cm³ of acetone are added to a solution of 10.5 g of a mixture of the A and B forms (about 15/85 in moles) of N-benzylquininium 1-(3-nitrophenyl)ethanesulphonate in 16 cm³ of acetone. The insoluble product is filtered off and then dissolved in 9 cm³ of water. 8.4 cm³ of an aqueous 1N hydrochloric acid solution and 1.15 g of (R)-(-)-phenylglycinol are added. The solution obtained is concentrated to dryness under reduced pressure (2.7 kPa) at 50° C. The residue obtained is extracted with 3 times 15 cm³ of acetonitrile under reflux. The organic phases are combined and concentrated to about 7 cm³; after cooling, the crystals are filtered off and dissolved in 7.5 cm³ of an aqueous 1N sodium hydroxide solution. The solution obtained is washed with 8 times 25 cm³ of diethyl ether, after which 60 cm³ of an aqueous 0.5M solution of potassium dihydrogenphosphate and 2.3 g of tetra-n-butylammonium hydrogensulphate are added. The mixture is extracted with 3 times 30 cm³ of methylene chloride. The combined organic phases are dried over magnesium sulphate and concentrated to dryness under reduced pressure (2.7 kPa) at 40° C. 2.8 g of the laevorotatory isomer of tetra-n-butylammonium 1-(3-nitrophenyl)ethanesulphonate are thus obtained in the form of an oil which is used as such in the subsequent syntheses.

d) laevorotatory isomer of tetra-n-butylammonium 1-(3-aminophenyl)ethanesulphonate:

0.2 g of 5% strength palladium on charcoal is added to a solution of 2.8 g of the laevorotatory isomer of tetra-n-butylammonium 1-(3-nitrophenyl)ethanesulphonate in 50 cm³ of ethanol. The suspension is stirred for 2 hours at a temperature of about 25° C. under a hydrogen atmosphere (100 kPa). The catalyst is filtered off and the filtrate is concentrated to dryness under reduced pressure (2.7 kPa) at 40° C. 2.8 g of the laevorotatory isomer of tetra-n-butylammonium 1-(3-aminophenyl)ethanesulphonate are thus obtained in the form of an oil, used as such in the subsequent syntheses.

NMR spectrum: (200 MHz; CDCl₃, B form)
δ (ppm):

| 0.98 | (t, J=7 Hz, 12H: —CH₃ of the butyl) |
| from 1.25 to 1.65 | (mt, 16H: —CH₂—CH₂—CH₃ of the butyl) |
| 1.65 | (d, J=7 Hz, 3H: —CH(CH₃)) |
| 2.95 | (mf, 2H: —NH₂) |
| 3.15 | (mt, 8H: >N—(CH₂—) of the butyl) |
| 3.91 | (q, J=7 Hz, 1H: —CH(CH₃)—) |
| 6.50 | (d, broad, J=8 Hz, 1H: —C₆H₄ (H4)) |
| 6.85 | (d, J=8 Hz, 1H: —C₆H₄ (H6)) |
| 6.86 | (s broad, 1H: —C₆H₄ (H2)) |
| 7.00 | (t, J=8 Hz, 1H: —C₆H₄ (H5)) |

APPLICATION EXAMPLE 2.7 g of the laevorotatory isomer of tetra-n-butylammonium 1-(3-aminophenyl)ethanesulphonate are added to a solution of 2.1 g of 2-{2-[(imidazolyl- 1)carboxamido]-N-(3-methoxyphenyl)acetamido}-N-methyl-N-phenyl-acetamide in 130 cm³ of toluene. The reaction mixture is stirred under reflux for 5 hours and then concentrated to dryness under reduced pressure (2.7 kPa) at 45° C. The residue is dissolved in 100 cm³ of methylene chloride and the solution obtained is washed with 50 cm³ of an aqueous 2N hydrochloric acid solution and then with twice 50 cm³ of water. The organic phase is dried over magnesium sulphate and concentrated to dryness under reduced pressure ( 2.7 kPa ) at 40° C. The crude product obtained is stirred for 30 minutes in 50 cm³ of diisopropyl ether. The insoluble product is filtered off and then dissolved in 6 cm³ of acetone. 1.2 g of potassium nonafluorobutanesulphonate dissolved in 3 cm³ of acetone are added, followed by 5 cm³ of diisopropyl ether. The insoluble gum is separated off and then stirred for 1 hour in 12 cm³ of a mixture of acetone and diisopropyl ether (50/50 by volume). The insoluble product is filtered off, washed with twice 5 cm³ of a mixture of acetone and diisopropyl ether (50/50 by volume) and then 4 times 5 cm³ of diisopropyl ether and is dried in air. 1.55 g of potassium (-)-1-{3-{3-[N-( 3-methoxyphenyl)-N-(N-methyl-N-phenylcarbamoylmethyl)carbamoylmethyl] ureido}phenyl}ethanesulphonate, melting at about 180° C., are thus obtained. $[\alpha]_D^{20}$=−5.0°±0.5 (C=0.888%; Methanol).

NMR spectrum: (300 MHz; DMSO d6: (−) form)
δ (ppm):

| 1.43 | [d, J=7 Hz, 3H: —CH(CH₃)—] |
| 3.18 | [broad s, 3H: —N(CH₃)—] |
| 3.60 | [mt, 1H: —CH(CH₃)—] |
| 3.65 | [broad d, J=5 Hz, 2H: —CO(CH₂)NH—] |
| 3.79 | (s, 3H, —OCH₃) |
| 4.09 | [mf, 2H: —CO(CH₂)N<] |
| 6.28 | [broad t, J=5 Hz, 1H: —NH—] |
| 6.86 | [d, J=7.5 Hz, 1H: —C₆H₄ (—H4) of the N-(3-Methoxyphenyl)] |
| from 6.95 to 7.15 | (mt, 4H: aromatics) |
| 7.17 | (broad s, 1H: —C₆H₄ (—H2) of the N—(3-methoxyphenyl)] |
| from 7.30 to 7.50 | (mt, 11H: aromatics) |
| 8.80 | (broad s, 1H: —CO—NH—Ar). |

2-{2-[(1-Imidazolyl)carboxamido]-N-( 3-methoxyphenyl)acetamido}-N-methyl-N-phenylacetamide can be prepared in the following manner: a solution of 3.1 g of 2-[2-amino-N-( 3-methoxyphenyl)acetamido]-N-methyl-N-phenylacetamide in 30 cm³ of anhydrous tetrahydrofuran is added to a solution of 3.0 g of N,N'-dimidazolecarbonyl in 30 cm³ of anhydrous tetrahydrofuran. The solution is stirred for 16 hours at a temperature of about 25° C. and then concentrated to dryness under reduced pressure (2.7 kPa) at 40° C. The residue is dissolved in 50 cm³ of ethyl acetate and the solution obtained is washed with 4 times 30 cm³ of water. The organic phase is dried over magnesium sulphate and then concentrated to dryness under reduced pressure (2.7 kPa) at 40° C. After recrystallization from ethyl acetate, 3.5 g of 2-{2-[( 1-imidazolyl)carboxamido]-N-( 3-methoxyphenyl)acetamido}-N-methyl-N-phenylacetamide, melting at 146° C., are obtained.

2-[2-Amino-N-( 3-methoxyphenyl)acetamido]-N-methyl-N-phenylacetamide can be prepared in the following manner: 1.3 g of hydrazine hydrate are added to a solution of 5.5 g of 2-[N-(3-methoxyphenyl)- 2-phthalimidoacetamido]-N-methyl-N-phenylacetamide in 60 cm³ of methanol. The reaction mixture is stirred under reflux for 30 minutes and, after cooling, 100 cm³ of water are added. The mixture is concentrated to about 100 cm³ and then brought to pH 9 with an aqueous 2N sodium hydroxide solution and extracted with twice 50 cm³ of ethyl acetate. The combined organic phases are washed with twice 50 cm³ of water, dried over magnesium sulphate and then concentrated to dryness under reduced pressure (2.7 kPa) at 40° C. 3.0 g of 2-[2-amino-N-(3methoxyphenyl)acetamido]-N-methyl-N-phenylacetamide are thus obtained in the form of an oil, which is used as such in the subsequent syntheses.

2-[N-(3-Methoxyphenyl)- 2-phthalimidoacetamido]-N-methyl-N-phenylacetamide can be prepared in the following manner: 10 cm³ of dimethylformamide are added to a suspension of 80.6 g of 2-[N-( 3-methoxyphenyl)-2-phthalimidoacetamido]acetic acid in 900 cm³ of 1,2-dichloroethane, after which 30.2 g of oxalyl dichloride are added over 1 hour. The mixture is stirred for 2 hours at a temperature of about 25° C., after which 58.6 g of N-methylaniline are added over 45° minutes. The reaction mixture is stirred for 2 hours at a temperature of about 25° C. washed with twice 500 cm³ of water and then with 300 cm³ of a saturated aqueous sodium bicarbonate solution, is dried over magnesium Sulphate and is concentrated to dryness under reduced pressure (2.7 kPa) at 40° C. The residue is stirred for one hour in 300 cm³ of diisopropyl ether and the insoluble product is filtered off, washed with 3 times 60 cm³ of diisopropyl ether and dried in air. 84 g of 2-[N-(3-methoxyphenyl)- 2-phthalimidoacetamido]-N-methyl-N-phenylacetamide, melting at 137° C., are thus obtained.

2-[N-(3-Methoxyphenyl)-2-phthalimidoacetamido]acetic acid can be prepared in the following manner: 74.0 g of trifluoroacetic acid are added to a solution of 42.0 g of tert-butyl 2-[N-( 3-methoxyphenyl)-2-phthalimidoacetamido]acetate in 500 cm³ of methylene chloride. The solution obtained is stirred under reflux for 5 hours and then concentrated to—dryness under reduced pressure (2.7 kPa) at 40° C. The residue is stirred for one hour in 100 cm³ of diisopropyl ether and the insoluble product is filtered off, washed with 3 times 40 cm³ of diisopropyl ether and dried in air. 36 g of 2-[N-(3-methoxyphenyl)- 2phthalimidoacetamido]acetic acid, melting at 203° C., are thus obtained.

tert-Butyl 2-[N-(3-methoxyphenyl)-2-phthalimidoacetamido]acetate can be prepared in the following manner: 14.9 g of an oily suspension (60 % by weight) of sodium hydride are added, over 30 minutes, to a solution of 96 g of N-(3-methoxyphenyl)-2-phthalimidoacetamide in 1000 cm³ of anhydrous tetrahydrofuran. The suspension is stirred for 4 hours at a temperature of about 20° C., after which 72.7 g of tert-butyl bromoacetate are added over 15 minutes. The reaction mixture is stirred for 16 hours at a temperature of about 25° C., hydrolyzed slowly with 50 cm³ of water and then concentrated to dryness under reduced pressure. The residue obtained is stirred for one hour in 400 cm³ of water and the insoluble product is filtered off, washed with 3 times 100 cm³ of water and twice 100 cm³ of diisopropyl ether and dried in air. 82.0 g of tert-butyl 2-[N-(3-methoxyphenyl)-2-phthalimidoacetamido]acetate, melting at 148° C., are thus obtained.

N-(3-Methoxyphenyl)-2-phthalimidoacetamide can be prepared in the following manner: 22.0 g of triethylamine followed by 48.0 g of 2-phthalimidoacetyl chloride dissolved in 300 cm³ of methylene chloride are added to a solution of 26.0 g of 3-methoxyaniline in 200 cm³ of methylene chloride, whilst keeping the temperature at about 20° C. The reaction mixture is stirred for 4 hours at this temperature and 800 cm³ of water are then added. The insoluble product is filtered off, washed with 3 times 100 cm³ of water and dried in air. 65.0 g of N-( 3-methoxyphenyl)-2-phthalimidoacetamide, melting at 171° C., are thus obtained.

2-Phthalimidoacetyl chloride can be prepared in accordance with the method described by W. Grassmann and E. Schulte-Uebbing, Chem. Ber., 83, 244–247, (1950).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. The laevorotatory isomers of alkylammonium 1-(3-aminophenyl)ethanesulphonates of formula:

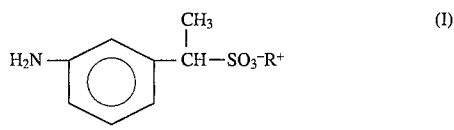

in which $R^+$ represents a tetraalkylammonium or trialkylphenylalkylammonium residue.

2. Process for the preparation of the compounds of formula (I) according to claim 1, which comprises the following stages:

a) action of an alkali metal sulphite on (RS)- 1-(1-bromoethyl)-3-nitrobenzene and conversion to the potassium salt to give potassium (RS)-1-(3-nitrophenyl)ethanesulphonate, b) conversion of the potassium salt obtained in a) into a mixture of the A and B forms of benzylquininium 1-(3-nitrophenyl)ethanesulphonate, separation of the A form and recovery of a mixture enriched in the B form, c) conversion of the benzylquininium salt, enriched in the B form, obtained in b) into potassium 1-(3-nitrophenyl)ethanesulphonate, thereafter into phenylglycinol 1-(3-nitrophenyl)ethanesulphonate, B form, and finally into the tetraalkylammonium or trialkylphenylalkylammonium 1-(3-nitrophenyl)-ethanesulphonate (laevorotatory isomer), d) reduction of the product obtained in c) to give the compound of formula (I), laevorotatory isomer.

3. Process according to claim 2, wherein stage a) is carried out in aqueous solution at a temperature of between 50° C. and 100° C.

4. Process according to claim 3, wherein the temperature is 80° C.

5. Process according to claim 3, wherein the recovery of the product is effected via a tetraalkylammonium or trialkylphenylalkylammonium salt.

6. Process according to claim 2, wherein stage b) is effected by means of an N-benzylquininium halide, in the presence of potassium dihydrogenphosphate in an aqueous medium at a temperature of between 10° C. and 30° C.

7. Process according to claim 6, wherein N-benzylquininium chloride is used.

8. Process according to claim 2, wherein sodium sulphite or potassium sulphite is used.

9. Process according to claim 2, wherein the potassium salt of stage c) is obtained by the action of potassium nonafluorobutanesulphonate in an inert solvent at a temperature of between 10° C. and 30° C.

10. Process according to claim 2, wherein in stage c), the phenylglycinol salt is obtained by the action of (R)-(-)-phenylglycinol in the presence of an acid, in an aqueous medium, at a temperature of between 10° C. and 30° C.

11. Process according to claim 2, wherein in stage c), the conversion to an alkylammonium salt or trialkylphenylalkylammonium salt is effected by means of a tetraalkylammonium or trialkylphenylalkylammonium salt, in an aqueous medium, at a temperature of 20° C.

12. Process according to claim 11, wherein a tetraalkylammonium hydrogensulphate or trialkylphenylalkylammonium hydrogensulphate is used.

13. Process according to claim 2, wherein the reduction is effected under hydrogen pressure, in the presence of a hydrogenation catalyst, in an inert solvent and at a temperature of about 25° C.

14. Process according to claim 13, wherein a hydrogen pressure of 100 kPa is used.

15. Process according to claim 2, for the preparation of the laevorotatory isomer of (tetra-n-butyl)ammonium 1-(3-aminophenyl)ethanesulphonate.

16. A method of using the compounds according to claim 1 for the preparation of enantiomers of the compounds of formula II:

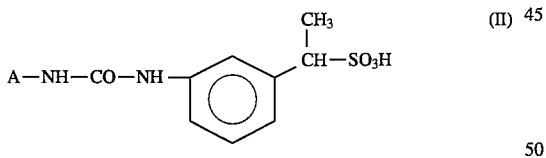
(II)

in which A represents

A) a —$CH_2$—CO—$NR_1R_2$ residue, in which $R_1$ represents one of the following radicals (a) phenyl optionally substituted by at least one substituent selected from among halogen atoms and alkyl, alkoxy, hydroxyl polyfluoroalkyl, nitro, alkylthio, alkoxycarbonyl, carboxyl, acylamino, methylenedioxy, polyfluoroalkoxy, trifluoromethylthio, phenoxy, phenyl, benzyl, phenylamino and $CONR_3R_4$ radicals, which may be identical or different, represent a hydrogen atom or an alkyl, phenyl (optionally substituted by at least one substituent selected from among halogen atoms and alkyl, alkoxy and alkylthio radicals), indanyl, cycloalkylalkyl, cycloalkyl or phenylalkyl radical or else $R_3$ and $R_4$ together with the nitrogen atom to which they are attached form a saturated or unsaturated monocyclic or polycyclic heterocyclic ring containing 4 to 9 carbon atoms and at lease one heteroatom selected from O, N and S and optionally substituted by one alkyl, alkoxy, alkoxycarbonyl, dialkylcarbamoyl or phenyl radical or, in combination with a carbon atom of the heterocyclic ring, by a spiromonocyclic ring having 4 or 5 members and optionally containing at least one heteroatom selected from O, S and N; b) pyridyl, c) isoquinolyl, d) quinolyl, e) quinoxalinyl (these heterocyclic rings being optionally substituted by at least one substituent selected from among alkyl and phenyl radicals and halogen atoms), f) alkyl, g) phenylalkyl, h) naphthyl, i) 5,6,7,8-tetrahydronaphthyl, j) 1,2,3,4-tetrahydronaphthyl, k) alkoxycarbonylalkyl or l) cycloalkyl, $R_2$ represents a —CH($R_5$)—CO—$R_6$ chain in which $R_5$ represents a hydrogen atom or an alkyl or alkoxycarbonyl radical or a phenyl radical (optionally substituted by at least one substituent selected from among halogen atoms and alkyl, alkoxy, alkylthio, nitro and amino radicals), and $R_6$ represents an alkoxy, cycloalkoxy (optionally substituted by at least one alkyl radical), cycloalkylalkoxy, phenylalkoxy, polyfluoroalkoxy cinnamyloxy radical and —$NR_3R_4$, B) a residue of formula:

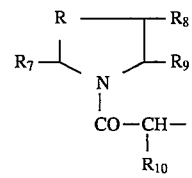

in which:

either R represents a methylene, ethylene, SO, $SO_2$ or CHOH radical or a sulphur atom, $R_7$ represents a pyridyl radical optionally substituted by at least one alkyl radical, a furyl radical optionally substituted by at least one alkyl radical, a thienyl radical optionally substituted by at least one alkyl radical, a quinolyl radical optionally substituted by at least one alkyl radical, a naphthyl radical optionally substituted by at least one alkyl radical, an indolyl radical optionally substituted by at least one alkyl radical or phenyl optionally substituted by at least one substituent selected from among halogen atoms and alkyl, alkoxy, hydroxyl, nitro, amino, monoalkylamino, dialkylamino, alkoxycarbonyl, —CO—$NR_{11}R_{12}$, —NH—CO—$CH_3$, trifluoromethyl or trifluoromethoxy radicals and $R_8$ represents a hydrogen atom, or R represents a methylene radical, $R_7$ represents a hydrogen atom and $R_8$ represents a phenyl radical, or R represents a $CHR_{13}$ radical, and $R_7$ and $R_8$ each represent a hydrogen atom, $R_9$ represents an alkoxycarbonyl, cycloalkoxycarbonyl, cycloalkylalkoxycarbonyl or —$CONR_{14}R_{15}$ radical or a phenyl radical optionally substituted by at least one substituent selected from among alkyl, alkoxy or hydroxyl radicals, $R_{10}$ represents a hydrogen atom or an alkyl radical, $R_{13}$ represents a phenyl radical, $R_{11}$ represents a hydrogen atom or one of the following radicals: alkyl, phenylalkyl or phenyl optionally substituted by at least one substituent selected from among halogen atoms and alkyl, alkoxy and alkylthio radicals, $R_{12}$ represents one of the following radicals: alkyl, phenylalkyl or phenyl optionally substituted by at least one substituent selected from among halogen atoms and alkyl, alkoxy and alkylthio radicals, or else $R_{11}$ and $R_{12}$, together with the nitrogen atom to which they are attached, form a monocyclic or polycyclic, saturated or unsaturated, heterocyclic ring which contains 4 to 9 carbon atoms and at least one heteroatom selected from O or N and is optionally substituted by at least one alkyl radical, $R_{14}$ represents a hydrogen atom or one of the following radicals: alkyl, cycloalkylalkyl, cycloalkyl, phenylalkyl or phenyl optionally substituted by at least one substituent selected from among halogen atoms and alkyl, alkoxy and alkylthio radicals, $R_{15}$ represents one of the following radicals: alkyl, cycloalkylalkyl, cycloalkyl, phenylalkyl or phenyl optionally substituted by at least one substituent selected from among halogen atoms and alkyl, alkoxy and alkylthio radicals, or else $R_{14}$ and $R_{15}$ together with the nitrogen atom to which they are attached form a monocyclic or polycyclic, saturated or unsaturated, heterocyclic ring which contains 4 to 9 carbon atoms and at least one heteroatom selected from O, N and S and is optionally substituted by at least one alkyl radical, C) a residue of formula:

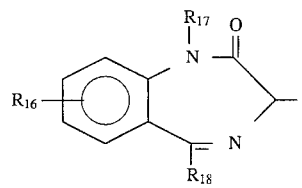

in which:

$R_{16}$ represents a hydrogen or halogen atom or an alkyl, alkylthio, nitro, hydroxyl or cyano radical, $R_{17}$ represents an alkyl radical or a —CH($R_5$)—CO—$R_6$ residue, $R_{18}$ represents a pyridyl radical or phenyl radical optionally substituted by at least one substituent selected from among halogen atoms and alkyl, alkoxy, hydroxyl, carboxyl, and nitro radicals, which comprises reacting a compound of the formula I according to claim 1 with a compound of formula

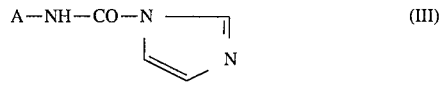

in which A is as defined above for formula II, wherein the reaction is carried out in an inert solvent, at a temperature of between about 20° C. and the boiling point of the solvent.

17. (Tetra-n-Butyl)-ammonium 1-(3-aminophenyl)ethanesulphonate (laevorotatory isomer).

* * * * *